United States Patent [19]
Lans et al.

[11] Patent Number: 6,050,820
[45] Date of Patent: Apr. 18, 2000

[54] INTRACORONALLY SUPPORTED PONTIC

[75] Inventors: Maris J. Lans, Centreville, Va.; Daniel E. Purvis, Indianapolis, Ind.

[73] Assignee: Eastflex Corp., Indianapolis, Ind.

[21] Appl. No.: 09/236,869

[22] Filed: Jan. 26, 1999

Related U.S. Application Data

[63] Continuation-in-part of application No. 08/855,319, May 13, 1997, Pat. No. 5,888,068.

[51] Int. Cl.[7] ........................... A61C 13/12; A61C 13/225
[52] U.S. Cl. ............................................................. 433/181
[58] Field of Search ...................... 433/180, 181, 433/182, 183, 190, 191

[56] References Cited

U.S. PATENT DOCUMENTS

| | | | |
|---|---|---|---|
| 1,211,494 | 1/1917 | Shaw | 433/181 |
| 2,087,047 | 7/1937 | Scheven | 433/181 |
| 2,826,814 | 3/1958 | Sappey et al. | 433/181 X |
| 4,445,862 | 5/1984 | Chiaramonte et al. | 433/181 X |
| 4,826,436 | 5/1989 | Shoher et al. | 433/183 X |
| 5,888,068 | 3/1999 | Lans et al. | 433/181 |

*Primary Examiner*—Nicholas D. Lucchesi

[57] ABSTRACT

The pontic support structure comprises a matrix folded to form a horizontal top portion and a vertical bottom portion. Opposed wings extend laterally on either side of the horizontal top portion. Opposed wings extend laterally on either side of the vertical bottom portion. The various wings engage corresponding slots formed in the existing adjacent teeth.

3 Claims, 3 Drawing Sheets

INTRACORONALLY SUPPORTED PONTIC

CROSS-REFERENCE TO RELATED APPLICATION

This application is a continuation-in-part of Ser. No. 08/855,319 filed May 13, 1997, now U.S. Pat. No. 5,888,068.

SUMMARY OF THE INVENTION

The present invention is directed to an intracoronally supported dental prosthesis. More particularly, the present invention teaches a means for supporting a pontic to replace a interdental missing teeth between two adjacent natural teeth. The invention further involves a unique anchoring system for maintaining the support structure between the two adjacent teeth as well as a system for forming the pontic around the support structure.

BACKGROUND OF THE INVENTION

Problems which are uniquely associated with the prosthetic replacement of missing teeth, as opposed to providing an entire bridgework, have long been recognized in dental technology. One of the principle difficulties has been in providing a satisfactory support structure for the pontic so that it is maintained correctly in position between the adjacent teeth. A further problem has been providing the pontic itself and attaching it to a satisfactory support structure between adjacent teeth, particularly in view of the natural movement which occurs between opposing and adjacent teeth in the chewing process.

The prior art systems for providing a prosthetic replacement between adjacent teeth have involved support structures that were either (1) fixed extra coronally to the back side of adjacent teeth or (2) supported by a "Maryland bridge", which fits inside the mouth. Either of these prior art practices add bulk dimension to the adjacent teeth or inner gum area. At best it is uncomfortable and difficult to maintain in hygienic condition. It is impossible to use in cases of tight occlusions.

Accordingly, there is a need to provide a prosthetic device and procedure which can be accomplished quickly and easily in a single sitting. There is a further need for a simplified device and procedure for fixing a pontic intracoronally between adjacent teeth so as to not impinge on the inner surface of the mouth.

Besides providing a simplified procedure and device which can be implemented in a single office visit, the present invention accomplishes these objectives and additionally provides a prosthesis pontic which does not impinge on the inner surface of the mouth and which can be altered as needed to accommodate changes in tissue contours.

It is a further object of the present invention to provide a prosthesis pontic support structure that can extend across a gap of two or more missing teeth, and be fixed intracoronally betweeen adjacent teeth so as to not impinge on the inner surface of the mouth.

DESCRIPTION OF THE PRIOR ART

In addition to that art cited by the Examiner in the parent application, the following prior art is considered relevant to the present invention:

U.S. Pat. No. 4,917,608 to Smith describes a cranial motion dental attachment for linking the interproximal walls of adjacent molded crowns while permitting relative movement between them.

U.S. Pat. No. 4,332,563 to Weissman describes a flexible dental retaining splint which is disposable in a channel extending between adjacent teeth, the retaining splint being formed of a wire core with a wire coil being wound around the core with the turns of the coil being in a juxtaposition.

U.S. Pat. No. 4,397,634 to Biggs describes surgical pins which can be used in dental and orthopedic surgery.

U.S. Pat. No. 3,015,888 to Dent describes a pontic structure and means for maintaining the pontic within the mouth without any visible evidence thereof.

U.S. Pat. No. 2,350,196 to Saffir describes pontic blocks which comprise a plurality of pontics secured together in a form suitable for incorporation in a denture.

U.S. Pat. No. 2,022,700 to Whitely describes an anchoring pin for pontics which includes protection against deleterious effects due to oxidation and presence of acids in the oral fluids.

DETAILED DESCRIPTION OF THE INVENTION

The present invention is directed to a new intracoronally supported prosthetic replacement for interdental missing teeth. It comprises a flat framework which can be stamped out of etched stainless steel. The framework has a central matrix portion and retention wing portions extending laterally on opposite sides of the matrix portion. Each wing portion is comprised of two or more parallel wings, which provide flexion relative to axis of the wings. The matrix portion includes parallel prongs to provide space between the prongs for displacement of bonding compositions, such as resin.

In applying the new device, parallel slots are drilled into the top and side of each tooth adjacent to the missing teeth. These slots correspond to the retention wing portions. By using a mold of the patient's dental arch, the dentist can form, shape, proportion and tint the pontic so that is specifically appropriate to the patient's specific need. This pontic superstructure is bonded to the infrastructure of the central matrix portion. The prosthetic device is then inserted into the intended space, the retention wing portions fitting into the corresponding slots provided in the adjacent teeth. When in place, the wings are bonded, sealed and covered with resin or other bonding composition, so that the inner and outer (i.e lingo proximal and buccal proximal) surfaces of the adjacent teeth are as they were before installation. The invention makes it possible to install the pontic during a single visit to the dentist; and the design of the invention is meant to receive all current dental restorative materials as the pontic superstructure. The invention can be fitted with silver alloy, hammered gold or hybird etched precious metal surfaces as well as resins for its pontic superstructure.

The retention wings of the invention allow for flexion about the axes. This allows one wing to be in compression while the other is in tension and provides translation forces that reduce the disruptive forces at the tooth-resin interface. The prongs of the matrix portion provides a space between the prongs for uniform resin displacement when the pontic is bonded to the matrix portion. This limits major voids formed at the bonded interfaces.

Figure 1:
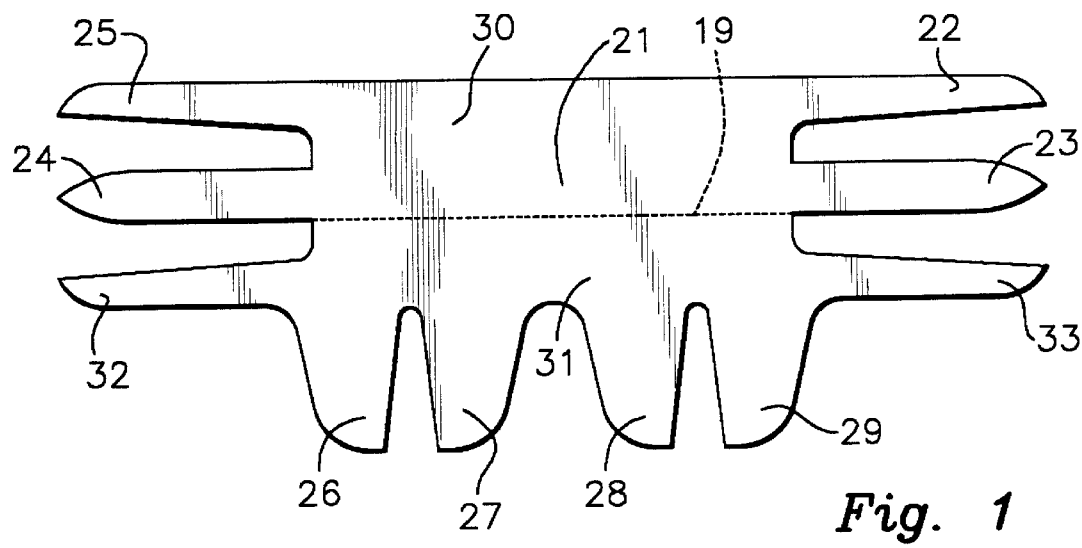
FIG. 1 illustrates the flat blank out of which the pontic support structure is formed.

The invention will however be more fully appreciated by having specific reference to the drawings which illustrate a preferred embodiment thereof Directing attention to FIG. 1 of the drawing, the pontic support structure is shown as the flat blank, that can be stamped or cut from a sheet of stainless steel or other appropriate material. It includes a matrix portion 21, provided with opposed parallel wings 22, 23, 24 and 25 and prongs 26, 27, 28, and 29 extending transverse to the opposed parallel wings.

Figure 2:
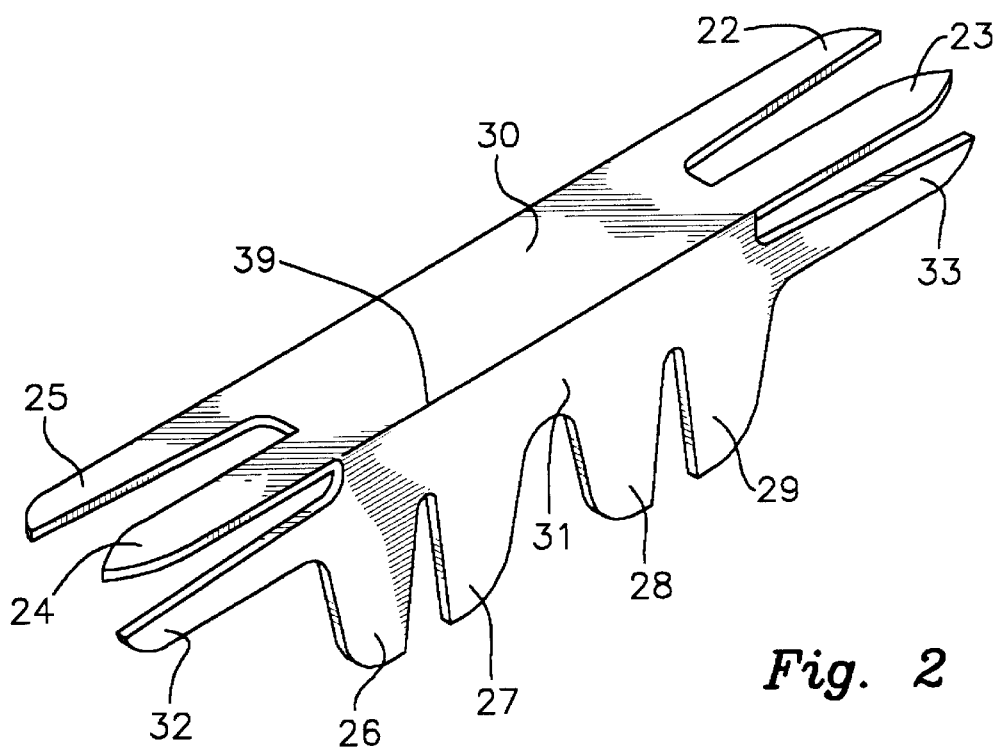
FIG. 2 illustrates the pontic support structure, the top portion of which has been bent into a horizontal position relative to the vertical bottom position.

As illustrated in FIG. 2, the top portion 30 of the blank is folded into a position horizontal to the vertical bottom portion 31, along fold line 39.

The flat blank of FIG. 1, also illustrates the engaging wings 32 and 33. When the blank is folded, as illustrated in FIG. 2 the engaging wings 32 and 33 are vertical extensions of lower portion 31, and at a right angle to the horizontal opposed parallel wings 22, 23, 24 and 25.

Figure 3:
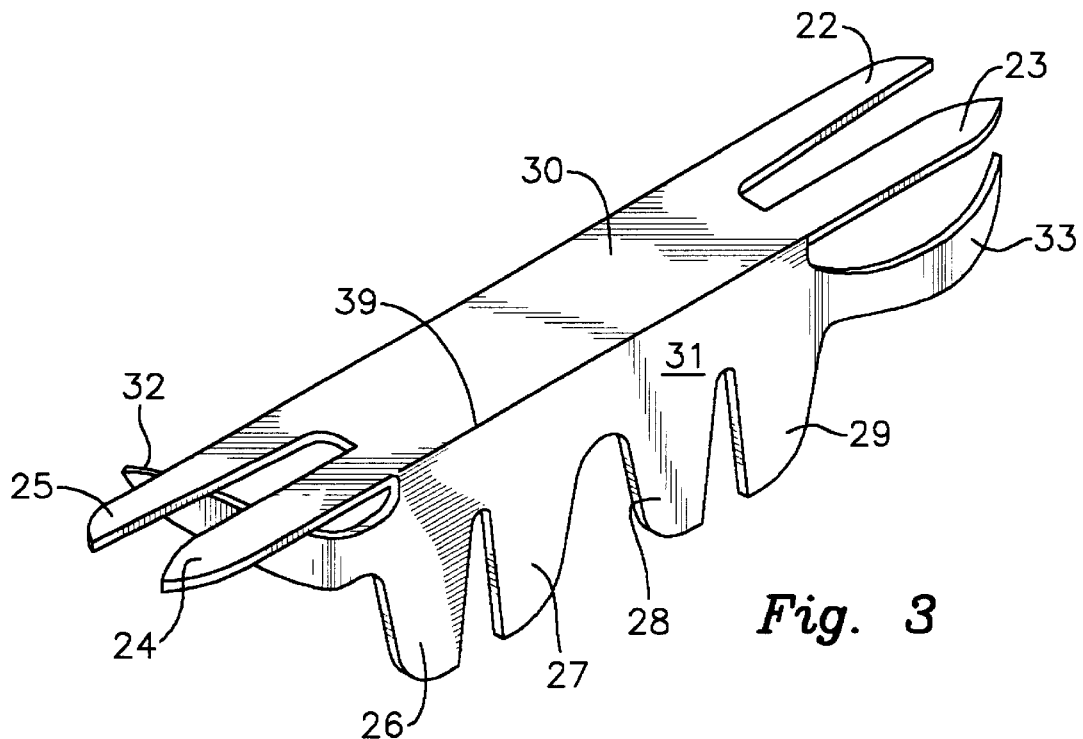
FIG. 3 illustrates the pontic support structure, the bottom engaging wings of which have been bent into an engaging relationship with the adjacent teeth.

FIG. 3 illustrates how the engaging wings 32 and 33, can be bent to engage the adjacent teeth. Specifically, wing 32 is bent to wrap around the inner, lingo proximal surface of one adjacent tooth, while wing 33 is bent to wrap around the outer, buccal proximal surface of the opposite adjacent tooth.

Figure 4:
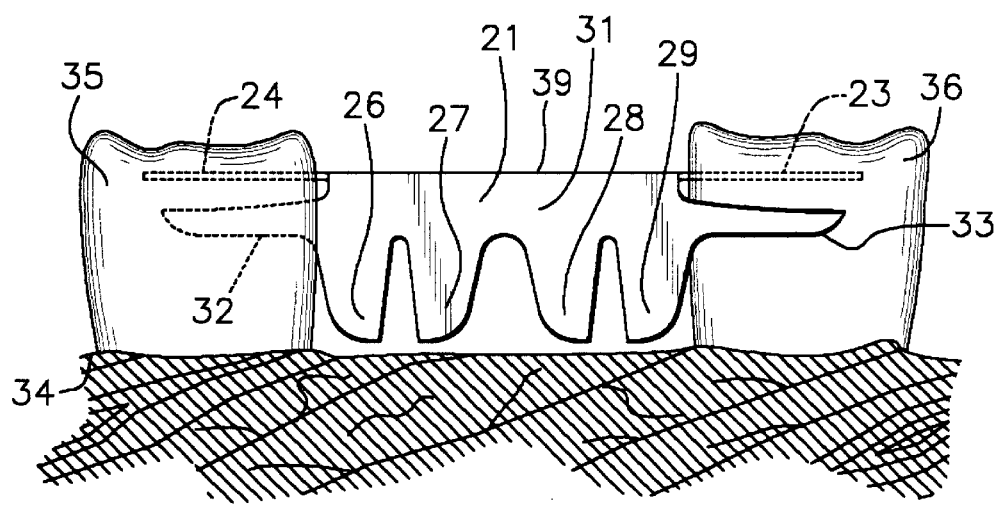
FIG. 4 illustrates in front plan view the pontic support structure in relation to the adjacent teeth.
Figure 5:
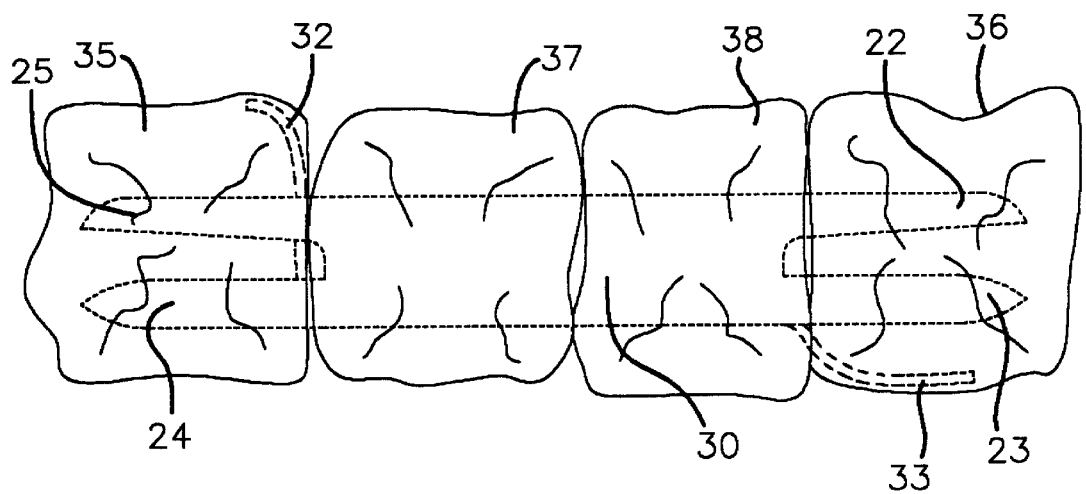
FIG. 5 illustrates in top plan view of the pontic and the pontic support structure in relation with the adjacent teeth.

FIG. 4 illustrates the pontic support structure in relation to and engaged with the adjacent teeth 35 and 36. The wings 22 and 23 fit into shallow parallel slots which have been drilled into the top surface adjacent tooth 36; wings 24 and 25 fit into shallow parallel slots which have been drilled into the top surface of adjacent tooth 35.

The pontic support structure of the present invention is used to span the gap of two or more missing teeth. This requires more points of flexible anchoring to the adjacent teeth than is required for a pontic filling the gap of a single missing tooth because a longer span must be supported. Therefore, in addition to the horizontal parallel wings 22, 23, 24 and 25, the pontic support structure of the present invention has the vertical parallel wings 32 and 33. Wing 32 fits into a shallow slot drilled into the lingo proximal surface of adjacent tooth 35. Wing 33 fits into a shallow slot drilled into the facial proximal surface of adjacent tooth 36. After appropriate pontic superstructures 37 and 38 have been formed on the matrix infrastructure 21, the various wings 22, 23, 24, 25, 32 and 33 are fitted into their corresponding slots on adjacent teeth 35 and 36, bonded, sealed and covered with resin or other bonding compositions. So when the pontic support structure has been installed, all top and side surfaces of the adjacent teeth will be substantially as they were before the installation.

It is axiomatic that any linear material folded to assume an "L" shaped cross section achieves an exponentially greater rigidity. Therefore, it will be understood that when the pontic support structure is installed, as above described, it provides great rigidity across its matrix portion 21 as a result of being folded along fold line 39 to assume an "L" shaped cross section. But the wings 22, 23, 24, 25, 32 and 33 are not folded and therefore provide the required degree of flexion between the pontic support structure and the adjacent teeth to which it is anchored.

It will be further understood that wings 22 and 23, are at opposite corners of the pontic support structure, or contralateral to each other. This contralateral positioning of wings 22 and 23 add to the stability provided by the horizontal parallel wings 22, 23, 24 and 25. But additionally, the vertical wings 32 and 33 permit a controlled vertical flexion of the pontic support structure.

It is an important aspect and advantage of the present invention, that it provides a central pontic support matrix 21, having a very rigid "L" shaped cross section where rigidity is required and yet it is anchored to the adjacent teeth by the relatively two dimensional wings 22, 23, 24 and 25, 32 and 33, which permit the desirable degree of flexion relative to the adjacent teeth, 35 and 36.

The intracoronally supported dental prosthesis of the present invention provides several advantages in addition to those described above, particularly with respect to pediatric and geriatric dentistry. In pediatric dentistry there is often a need for space management in the primary and secondary dentition. The present invention without modification can be used to fabricate fixed spaced maintenance appliances. Due to the refractive sizing, the invention can also be used in the fabrication of space regaining appliances. The advantage of the present invention over existing prior art in pediatric applications is that in the majority of prior art appliances the missing tooth space is first filled by a removable acrylic appliance which can be easily lost and which requires that the adjacent teeth be stripped to accommodate bands which are often necessary to retain the appliance. Because there is no visible metallic component in the present invention, aesthetics are far more acceptable to children as well as parents. Further, the present invention requires only that the support structure be suspended between the adjacent teeth and therefore does not bear down on the gingival tissue. Prior art devices in which pressure is exerted against gingival tissues can be uncomfortable for the patient in cases where an expected tooth is erupting beneath. Further, the cost of replacing a lost or removable retainer can increase the overall cost of orthodontic treatment. In children with handicaps from gross physical motor deficiencies to mild speech impediments, the fixed nature of the present invention is an obvious improvement over any removable appliance. Because the pontic can be easily modified and/or repaired, changes in gingival contour can be accommodated without extensive procedures. Identification chips can be placed inside the prosthesis of the invention to aid in the identification of lost children or for forensic investigations.

With regard to geriatric applications, conventional crowns and bridges usually require several appointments with the dentist, multiple local anesthetic injections and reduction of the enamel surface of the teeth and disruption of the pericoronal gingival attachment. The stresses of these procedures are often contra-indicated for the geriatric or medically compromised population. A shorter procedural time with the dentist lowers the cost of the procedure. The present invention can also be utilized as a periodontal splinting appliance to help stabilize the supporting teeth without excessive torque that would be unavoidable with a removable or conventionally fixed pontic and can be used in conjunction with the periodontal splint.

Because of the atrophy of the pulp chamber and formation of secondary dentin in older patients, the need for local anesthesia is often unnecessary in accordance with the procedure of the present invention as it requires only very conservative preparations. Fluoride releasing composites can be utilized to minimize the reduction of carries. This is an option that is not available with conventional procedures and appliances. Children can also benefit from the fluoride releasing composites. The procedure allows for the improvement of the contact point between the pontic and the adjacent supporting teeth by the ability to bond to the supporting teeth in a dynamic manner. This is achieved by bonding the teeth during occusal loading. Conventional bridges are cast or fabricated for a passive fit. Supporting teeth cannot move during the prior art occusal loading regardless of how heavy the cementation force is. The attachment system of the invention allows the pontic and support structure to move in relation to the occusal load because the resin is not completely set until it is cured. The procedure for bonding the support structure allows the dentist to fine tune the position of the pontic during the actual placement, which is something that conventional bridgework does not allow. Unique to the present invention is the occusal loading during bonding, placing the root surface of the supporting tooth on the pontic side in tension. Tension promotes osteoblastic activity which in turn promotes bone growth as opposed to conventional bridges which reduce the amount of bone because of gingival destruction. The present invention is therefore a constructive procedure because it improves interproximal contact, and promotes bone growth during its service in the patient's mouth, whereas the conventional bridge is destructive to the contacts and supporting bone, and gingival margins.

Further because of the osteoblastic activity associated with the present invention, an implant placed underneath it will be more rapidly and completely osteo-integrated thereby reducing the healing time significantly. Because the present invention is suspended over the implant site, there is no unfavorable pressure being directly exerted upon the pontic and the freshly healing gingival tissues, thereby greatly adding to patient comfort and the improved healing of the site of the surgery.

It should be noted that in performing the process of this invention, the pontic can be formed in situ around the support structure that is already intracoronally affixed to the adjacent teeth, or alternatively the pontic can be formed out of the mouth around the support structure, and the entire prosthetic device then installed between two adjacent teeth as described above. In the latter process, which is the one preferred in most circumstances, a mold is made of the dental arch including the gap formed by the missing tooth. Working with the mold, a pontic which is perfectly calculated for the gap can be formed in the laboratory using the latest and best techniques and materials with the support structure imbedded therein. When it is completed, it is then installed in the patient's mouth which does not take much of the patient's or dentist's time The process requires two visits to the dentist (i.e. (1) to cast the mold (2) to install the prosthetic device). However, in some circumstances where it may be necessary to have an immediate replacement of a mising tooth, the pontic can be formed in situ on the installed support structure all in one sitting. It will of course be appreciated that the cast pontic can then be finally configured by typical grinding techniques both to facilitate its bite and interaction with other teeth and its appearance.

Other modifications and alternatives to the herein described procedures and components will be apparent to those of ordinary skill this art and are considered to fall within the scope of the claims defining this invention.

What is claimed:

1. A dental prosthesis support structure for receiving and supporting a pontic and attaching it intracoronally between a pair of existing teeth, said support structure comprising a matrix folded to form a horizontal top portion and a vertical bottom portion, opposed wings extending laterally on either side of said horizontal top portion for engagement within corresponding slots formed in the said pair of existing teeth, opposed wings extending laterally on either side of the said vertical bottom portion for engagement within corresponding slots formed in the said existing teeth.

2. The dental prosthesis support structure of claim 1, wherein the opposed wing extending laterally from one side of the vertical bottom portion is bent to engage a slot formed in the inner side of the adjacent tooth, and the opposed wing extending laterally from the opposite side of the vertical bottom portion is bent to engage a slot formed in the outer side of the adjacent tooth.

3. The dental prosthesis support structure of claim 1, wherein the vertical bottom portion includes prongs extending transverse to the opposed parallel wings of the horizontal top portion.

* * * * *